United States Patent
Harris

(10) Patent No.: US 7,797,057 B2
(45) Date of Patent: Sep. 14, 2010

(54) MEDICAL PADDLE LEAD AND METHOD FOR SPINAL CORD STIMULATION

(75) Inventor: Charmaine K. Harris, Woodbury, MN (US)

(73) Assignee: Medtronic, Inc., Minneapolis, MN (US)

(*) Notice: Subject to any disclaimer, the term of this patent is extended or adjusted under 35 U.S.C. 154(b) by 641 days.

(21) Appl. No.: 10/691,859

(22) Filed: Oct. 23, 2003

(65) Prior Publication Data

US 2004/0260310 A1 Dec. 23, 2004

Related U.S. Application Data

(60) Provisional application No. 60/420,570, filed on Oct. 23, 2002, provisional application No. 60/508,107, filed on Oct. 2, 2003.

(51) Int. Cl.
*A61N 1/05* (2006.01)
(52) U.S. Cl. .................................................. 607/117
(58) Field of Classification Search .................. 607/117, 607/116, 46; 600/377
See application file for complete search history.

(56) References Cited

U.S. PATENT DOCUMENTS

| | | | |
|---|---|---|---|
| 3,605,750 A | 9/1971 | Sheridan et al. | |
| 3,646,940 A | 3/1972 | Timm et al. | |
| 3,724,467 A | 4/1973 | Avery et al. | |
| 4,141,365 A | 2/1979 | Fischell et al. | |
| 4,285,347 A | 8/1981 | Hess | |
| 4,379,462 A | 4/1983 | Borkan et al. | |
| 4,735,208 A | 4/1988 | Wyler et al. | |
| 4,800,898 A | 1/1989 | Hess et al. | |
| 4,817,613 A | 4/1989 | Jaraczewski et al. | |
| 4,903,702 A * | 2/1990 | Putz ........................... | 600/377 |
| 5,034,005 A | 7/1991 | Appling | |
| 5,042,463 A * | 8/1991 | Lekholm ...................... | 607/129 |
| 5,054,492 A | 10/1991 | Scribner et al. | |
| 5,121,754 A | 6/1992 | Mullett | |
| 5,249,574 A | 10/1993 | Bush et al. | |
| 5,255,691 A | 10/1993 | Otten | |
| 5,374,286 A | 12/1994 | Morris | |
| 5,412,707 A | 5/1995 | Hoeks | |
| 5,417,719 A | 5/1995 | Hull et al. | |
| 5,456,705 A | 10/1995 | Morris | |

(Continued)

FOREIGN PATENT DOCUMENTS

EP 0576075 A1 12/1993

(Continued)

OTHER PUBLICATIONS

Manual: "Surgical Lead Kits—Directions for Use", *Advanced Neuromodulation Systems, Inc.*, Dec. 2003, p. 1-13.

*Primary Examiner*—Carl H Layno
*Assistant Examiner*—Alyssa M Alter
(74) *Attorney, Agent, or Firm*—Fredrikson & Bryon, P.A.

(57) ABSTRACT

A medical lead for electrical stimulation or sensing. The medical lead has a generally flat paddle on the distal end of the lead body. An electrode array is provided on the paddle. The electrode array having directional electrical field properties relative to the first and major surfaces of the paddle (e.g., the electrodes are exposed through only one of the major surfaces). An orientation marker for determining orientation of the lead, with the orientation marking including fluoroscopically viewable material.

5 Claims, 18 Drawing Sheets

U.S. PATENT DOCUMENTS

| | | | |
|---|---|---|---|
| 5,473,812 A | 12/1995 | Morris et al. | |
| 5,474,558 A | 12/1995 | Neubardt | |
| 5,485,845 A | 1/1996 | Verdonk et al. | |
| 5,509,924 A | 4/1996 | Paspa et al. | |
| 5,669,882 A | 9/1997 | Pyles | |
| 5,701,900 A | 12/1997 | Shehada et al. | |
| 5,730,754 A | 3/1998 | Obenchain | |
| 5,843,148 A | 12/1998 | Gijsbers et al. | |
| 5,846,199 A | 12/1998 | Hijlkema et al. | |
| 5,876,408 A * | 3/1999 | Alt et al. | 606/129 |
| 5,902,236 A | 5/1999 | Iversen | |
| 5,908,413 A | 6/1999 | Lange et al. | |
| 6,010,493 A | 1/2000 | Snoke | |
| 6,024,702 A | 2/2000 | Iversen | |
| 6,036,682 A | 3/2000 | Lange et al. | |
| 6,055,456 A | 4/2000 | Gerber | |
| 6,066,165 A | 5/2000 | Racz | |
| 6,083,167 A | 7/2000 | Fox et al. | |
| 6,104,960 A | 8/2000 | Duysens et al. | |
| 6,179,788 B1 | 1/2001 | Sullivan | |
| 6,185,463 B1 * | 2/2001 | Baudino | 607/119 |
| 6,205,361 B1 | 3/2001 | Kuzma et al. | |
| 6,233,488 B1 | 5/2001 | Hess | |
| 6,236,892 B1 | 5/2001 | Feler | |
| 6,249,707 B1 | 6/2001 | Kohnen et al. | |
| 6,272,370 B1 * | 8/2001 | Gillies et al. | 600/411 |
| 6,273,858 B1 | 8/2001 | Fox et al. | |
| 6,277,094 B1 | 8/2001 | Schendel | |
| 6,277,108 B1 | 8/2001 | McBroom et al. | |
| 6,308,103 B1 | 10/2001 | Gielen | |
| 6,309,401 B1 | 10/2001 | Redko et al. | |
| 6,360,750 B1 | 3/2002 | Gerber et al. | |
| 6,415,187 B1 | 7/2002 | Kuzma et al. | |
| 6,438,401 B1 | 8/2002 | Cheng et al. | |
| 6,512,958 B1 | 1/2003 | Swoyer et al. | |
| 6,522,932 B1 | 2/2003 | Kuzma et al. | |
| 6,553,264 B2 | 4/2003 | Redko et al. | |
| 6,587,733 B1 | 7/2003 | Cross, Jr. et al. | |
| 6,606,521 B2 | 8/2003 | Paspa et al. | |
| 6,697,677 B2 | 2/2004 | Dahl et al. | |
| 6,754,539 B1 | 6/2004 | Drees et al. | |
| 6,895,283 B2 * | 5/2005 | Erickson et al. | 607/117 |
| 2001/0025192 A1 | 9/2001 | Gerber et al. | |
| 2002/0022873 A1 | 2/2002 | Erickson et al. | |
| 2002/0035377 A1 | 3/2002 | Bardy et al. | |
| 2002/0035378 A1 | 3/2002 | Bardy et al. | |
| 2002/0035379 A1 | 3/2002 | Bardy et al. | |
| 2002/0035381 A1 | 3/2002 | Bardy et al. | |
| 2002/0042642 A1 | 4/2002 | Gerber | |
| 2002/0052636 A1 | 5/2002 | Bardy et al. | |
| 2002/0107549 A1 | 8/2002 | Bardy et al. | |
| 2002/0111661 A1 * | 8/2002 | Cross et al. | 607/117 |
| 2002/0128700 A1 | 9/2002 | Cross, Jr. | |
| 2002/0147485 A1 | 10/2002 | Mamo et al. | |
| 2003/0028147 A1 | 2/2003 | Aves et al. | |
| 2003/0036787 A1 | 2/2003 | Redko et al. | |
| 2003/0055476 A1 | 3/2003 | Vinup et al. | |
| 2003/0069623 A1 | 4/2003 | Stypulkowski | |
| 2003/0088301 A1 * | 5/2003 | King | 607/117 |
| 2003/0135253 A1 | 7/2003 | Kokones et al. | |
| 2003/0139782 A1 * | 7/2003 | Duncan et al. | 607/48 |
| 2003/0204228 A1 | 10/2003 | Cross, Jr. et al. | |
| 2004/0002643 A1 | 1/2004 | Hastings et al. | |
| 2005/0004638 A1 * | 1/2005 | Cross, Jr. | 607/117 |

FOREIGN PATENT DOCUMENTS

| | | |
|---|---|---|
| EP | 0607688 A1 | 7/1994 |
| EP | 0745891 A2 | 12/1996 |
| EP | 0778048 A1 | 6/1997 |
| EP | 1048270 A1 | 11/2000 |
| EP | 1048271 A2 | 11/2000 |
| EP | 1048317 A2 | 11/2000 |
| EP | 1048321 A2 | 11/2000 |
| EP | 1048321 A3 | 3/2001 |
| EP | 1181947 A2 | 2/2002 |
| EP | 1181947 A3 | 8/2002 |
| EP | 1048317 A3 | 3/2003 |
| EP | 0778048 B1 | 9/2003 |
| GB | 2132895 A | 7/1984 |
| WO | WO 96/39081 A1 | 12/1996 |
| WO | WO 99/55411 A3 | 11/1999 |
| WO | WO 99/56817 A1 | 11/1999 |
| WO | WO 99/56818 A1 | 11/1999 |
| WO | WO 01/00274 A1 | 1/2001 |
| WO | WO 01/24872 A1 | 4/2001 |
| WO | WO 01/58519 A1 | 8/2001 |
| WO | WO 02/13903 A2 | 2/2002 |
| WO | WO 02/072192 A2 | 9/2002 |
| WO | WO 02/087678 A1 | 11/2002 |
| WO | WO 03/011361 A2 | 2/2003 |
| WO | WO 03/013650 A1 | 2/2003 |
| WO | WO 03/018110 A2 | 3/2003 |
| WO | WO 03/018111 A2 | 3/2003 |
| WO | WO 03/018112 A2 | 3/2003 |
| WO | WO 03/018127 A2 | 3/2003 |
| WO | WO 03/018130 A2 | 3/2003 |
| WO | WO 03/039656 A1 | 5/2003 |
| WO | WO 03/059440 A2 | 7/2003 |
| WO | WO 03/090851 A2 | 11/2003 |

* cited by examiner

MEDICAL PADDLE LEAD AND METHOD FOR SPINAL CORD STIMULATION

RELATED APPLICATIONS

This application claims priority to provisional U.S. Application Ser. No. 60/420,570, filed Oct. 23, 2002, and provisional U.S. Application Ser. No. 60/508,107, filed Oct. 2, 2003.

FIELD OF THE INVENTION

This application relates generally to medical leads for electrical stimulation or sensing and methods of use thereof, and more particularly to a paddle-style lead, for example, for spinal cord stimulation and methods of use thereof.

BACKGROUND OF THE INVENTION

Currently anesthesiologists may non-surgically implant a percutaneous versions of medical leads for spinal cord stimulation (SCS) with Touhy needles. Typically, percutaneous versions of medical leads have been various standard cylindrical styles rather than flattened paddle style leads, which tend to be surgically implanted by surgeons with the associated discomfort, expense and inconvenience of surgical procedures. Paddle-style leads, however, are at least perceived to be more stable in their location after implantation.

U.S. Pat. No. 6,309,401 and EP Publication No. 1 048 270 discloses an apparatus for percutaneous implant of a paddle style lead in which a needle having a flattened cross section is used. U.S. Pat. No. 6,309,401 and EP 1 048 270 are incorporated herein by reference in their entirety, and particular note is made of the flattened needle, which may be used with certain exemplary embodiments of the medical lead disclosed herein.

There is a well-known need or desire for a paddle-style lead that can be implanted without performing a surgical procedure, such as a laminectomy or laminotomy.

SUMMARY OF EXEMPLARY EMBODIMENTS OF THE INVENTION

A medical lead is provided for electrical stimulation or sensing. Exemplary embodiments of the medical lead are adapted to facilitate repositioning, withdrawal or explanting the medical lead, as well as using the features of a flat lead paddle to anchor the lead to the connective tissue. Exemplary embodiments of the medical lead are adapted for percutaneous introduction of the medical lead through an introducer needle, such as a flattened Tuohy needle.

An exemplary medical lead has a generally flat paddle on the distal end of the lead body. An electrode array is provided on the paddle, with the electrode array displaced along the length of the paddle toward the distal end. The length of the paddle between the electrode array and proximal end of the paddle allow the electrode array may be advanced into position for electrical stimulation or sensing with a proximal portion of the flat paddle extending through connective tissue, such as the ligamentum flavum. Because the edge formed by the proximal end of the paddle is not pushed through the connective tissue, it does not interfere with repositioning, withdrawing or explanting the medical lead. In addition, the flat features of the paddle may be used to anchor the lead to the connective tissue.

A first exemplary embodiment of the medical lead comprises a generally round or tubular lead body having proximal and distal ends, and at least one electrical conductor extending between the proximal and distal ends. A connector is provided on the proximal end of the lead body in electrical communication with the electrical conductor. A generally flat paddle on the distal end of the lead body has an electrode array comprising at least one electrode in electrical communication with the electrical conductor. The paddle has proximal and distal ends and a length extending between the proximal and distal ends. The electrode array is displaced along the length of the paddle toward the distal end, whereby the electrode array may be advanced into position for electrical stimulation or sensing with the flat paddle extending through connective tissue, such as the ligamentum flavum.

A second exemplary embodiment of the medical lead generally comprises a generally round or tubular lead body having proximal and distal ends, and at least one electrical conductor extending between the proximal and distal ends. A connector is provided on the proximal end of the lead body in electrical communication with the electrical conductor. A generally flat paddle on the distal end of the lead body has an electrode array comprising at least one electrode in electrical communication with the electrical conductor. The paddle has proximal and distal ends and a length extending between the proximal and distal ends. The electrode array is displaced along the length of the paddle toward the distal end such that the portion of the flat paddle proximal of the electrode array has a length of at least 1½ inches (40 mm).

In an exemplary aspect of the first and second exemplary embodiments, a medical lead system is provided comprising the medical lead and an anchor adapted for clamping the flat paddle and anchoring it to connective tissue, such as the ligamentum flavum. For example, the anchor may comprise two clamping jaws adapted to clamp the major surfaces of the flat paddle therebetween. One of the clamping arms may optionally be provided with at least one rib, e.g., a plurality such as three ribs, adapted to engage the flat paddle and retain it in position. The clamping arms may be designed to be separable, with the clamping arms being provided with mating knobs and cavities or other features for attaching the clamping arms together.

A third exemplary embodiment is a medical lead system that generally comprises a medical lead and an anchor. The medical lead comprises a generally round or tubular lead body having proximal and distal ends, and at least one electrical conductor extending between the proximal and distal ends. A connector is provided on the proximal end of the lead body in electrical communication with the electrical conductor. A generally flat paddle on the distal end of the lead body has an electrode array comprising at least one electrode in electrical communication with the electrical conductor. The paddle has proximal and distal ends and a length extending between the proximal and distal ends, with the electrode array optionally being displaced along the length of the paddle toward the distal end. The anchor is configured for attachment to the paddle to anchor the paddle relative to biological tissue.

In a fourth exemplary embodiment, a method generally comprises percutaneously introducing distal end of the paddle with an introducer needle generally through connective tissue, such as the ligamentum flavum, into or adjacent a desired stimulation or sensing site, such as epidural space for spinal cord stimulation, in a patient with the proximal end of the paddle left extending out from the connective tissue. The flat paddle may be anchored to the connective tissue. The paddle may be repositioned or removed without cutting through or dissecting the connective tissue (e.g., ligamentum flavum).

In an exemplary embodiment of an implantation method, a medical lead is used having a generally flat paddle having proximal and distal ends and a length extending between the proximal and distal ends, and an electrode array comprising at least one electrode, with the electrode array being displaced along the length of the paddle toward the distal end. The method of this exemplary embodiment generally comprises (a) percutaneously introducing distal end of the paddle generally anteriorly through the ligamentum flavum into an epidural space of a patient through a needle with the proximal end of the paddle remaining on the posterior side of the ligamentum flavum; and anchoring the paddle to the posterior side of the ligamentum flavum.

An additional exemplary embodiment includes a medical lead having an identification marker for determining orientation or identifying the lead. For example, the marker may provide a definite indication of the direction of the lead (which way it is facing), and/or be coded to identify the model or serial number of a lead.

In yet another exemplary embodiment of a medical lead, the lead generally comprises a generally flat paddle on the distal end of the lead body. The paddle has first and second major surfaces, and an electrode array comprising at least one electrode in electrical communication with the electrical conductor, the electrode array having directional electrical field properties relative to the first and major surfaces of the paddle. An orientation marker is provided for determining orientation of the lead, the orientation marking including fluoroscopically viewable material.

In still another exemplary embodiment of a medical lead, the lead generally comprises a lead body having proximal and distal ends, and at least one electrical conductor extending between the proximal and distal ends. A connector is on the proximal end of the lead body in electrical communication with the electrical conductor. A generally flat paddle is provided on the distal end of the lead body. The paddle has proximal and distal ends, first and second major surfaces, and a length extending between the proximal and distal ends. An electrode array is provided on the paddle comprising at least one electrode in electrical communication with the electrical conductor, the electrode array having directional electrical field properties relative to the first and second major surfaces. An orientation marker is provided for determining orientation of the lead. The orientation marking includes fluoroscopically viewable material.

Yet another exemplary embodiment is a combination or set comprising a paddle-style medical lead and a flattened needle. Preferably the combination further includes a plastic or elastomeric stylet that is cable of being withdrawn from the needle even if the needle has been subjected to plastic deformation.

Still another exemplary embodiment is a system comprising a medical lead and an implantable pulse generator. The system preferably includes at least one or two external programmer(s), such a physician programmer and a patient programmer.

These and other features are described hereinafter or in the drawings.

DETAILED DESCRIPTION OF EXEMPLARY EMBODIMENTS

Figure 1:
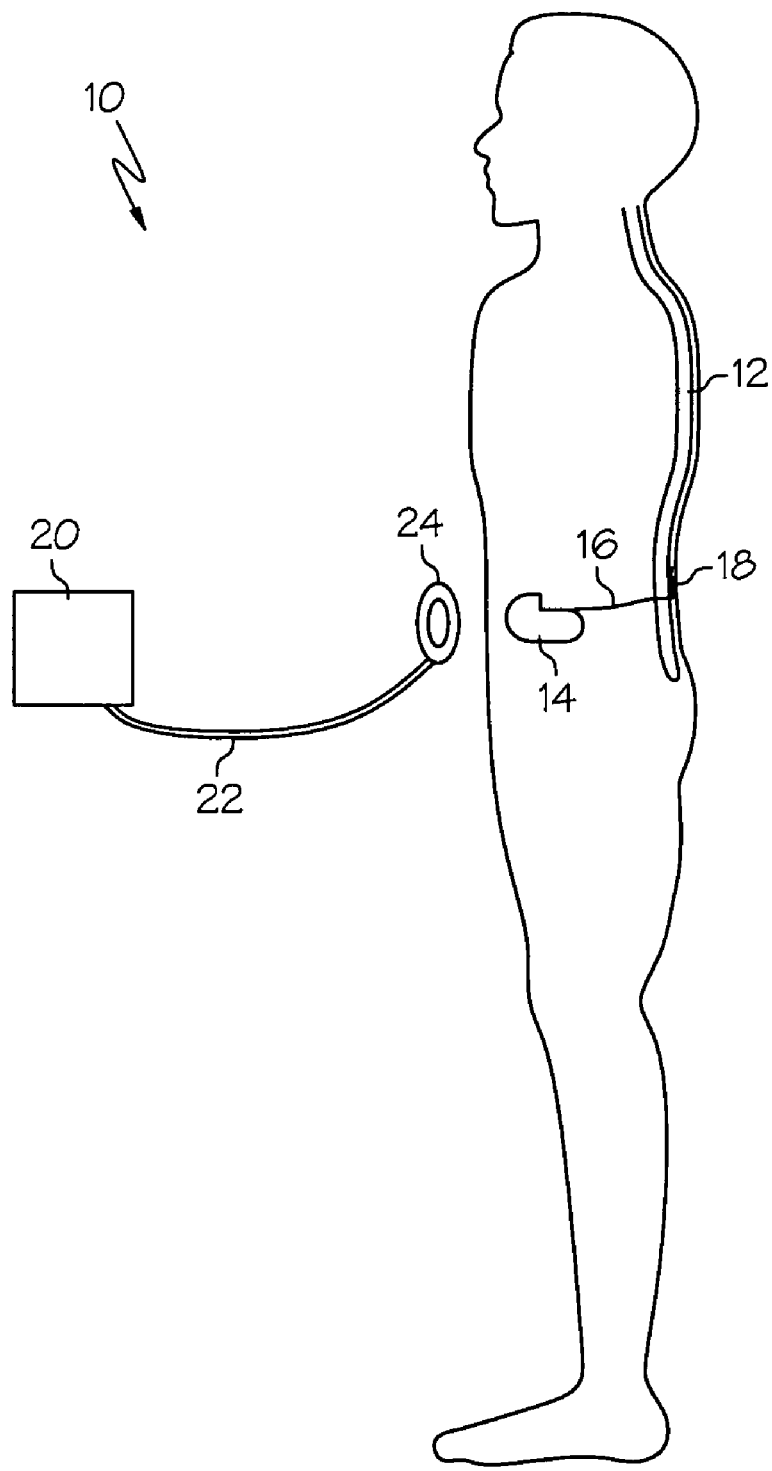
FIG. 1 is a schematic view of an exemplary embodiment of a system including a medical lead, implantable pulse generator (IPG) and programmer.

FIG. 1 is a schematic view of a patient 10 having an implant of a neurological stimulation system employing the present invention to stimulate spinal cord 12 of the patient. The preferred system employs implantable pulse generator (IPG) 14 to produce a number of independent stimulation pulses which are sent to spinal cord 12 by insulated lead 16 and coupled to the spinal cord by electrodes located at point 18. An extension, which includes a conductor, may also be used to electrically connect the IPG to the lead 16.

Implantable pulse generator 14 may be, for example, a neurostimulator, such as the neurostimulators available under the trade designations "Model 7425 Itrel™ 3 Neurostimulator" or "Model 7427 Synergy™ Neurostimulator," both available from Medtronic, Inc., Minneapolis, Minn. Exemplary embodiments of such implantable pulse generators 14 typically include a battery or other power source, a processor, and a connector header for connection of a lead or lead extension to the IPG, as well as a telemetry antenna to allow communication with the IPG to or from an external device.

This exemplary system may employ a programmer 20, which is coupled via conductor 22 to radio frequency antenna 24. This permits attending medical personnel to select the various pulse output options after implant using radio frequency communications. While the exemplary system employs fully implanted elements, systems employing partially implanted generators and radio-frequency coupling may also practice the present invention. The system may also include a patient programmer (similar at the schematic level to the programmer 20) allowing the patient to select or modify the stimulation therapy program.

While the preferred exemplary system employs fully implanted elements, systems employing partially implanted generators and radio-frequency coupling may also be used (e.g., similar to products sold by Medtronic, Inc. under the trademarks X-trel and Mattrix).

Figure 2:
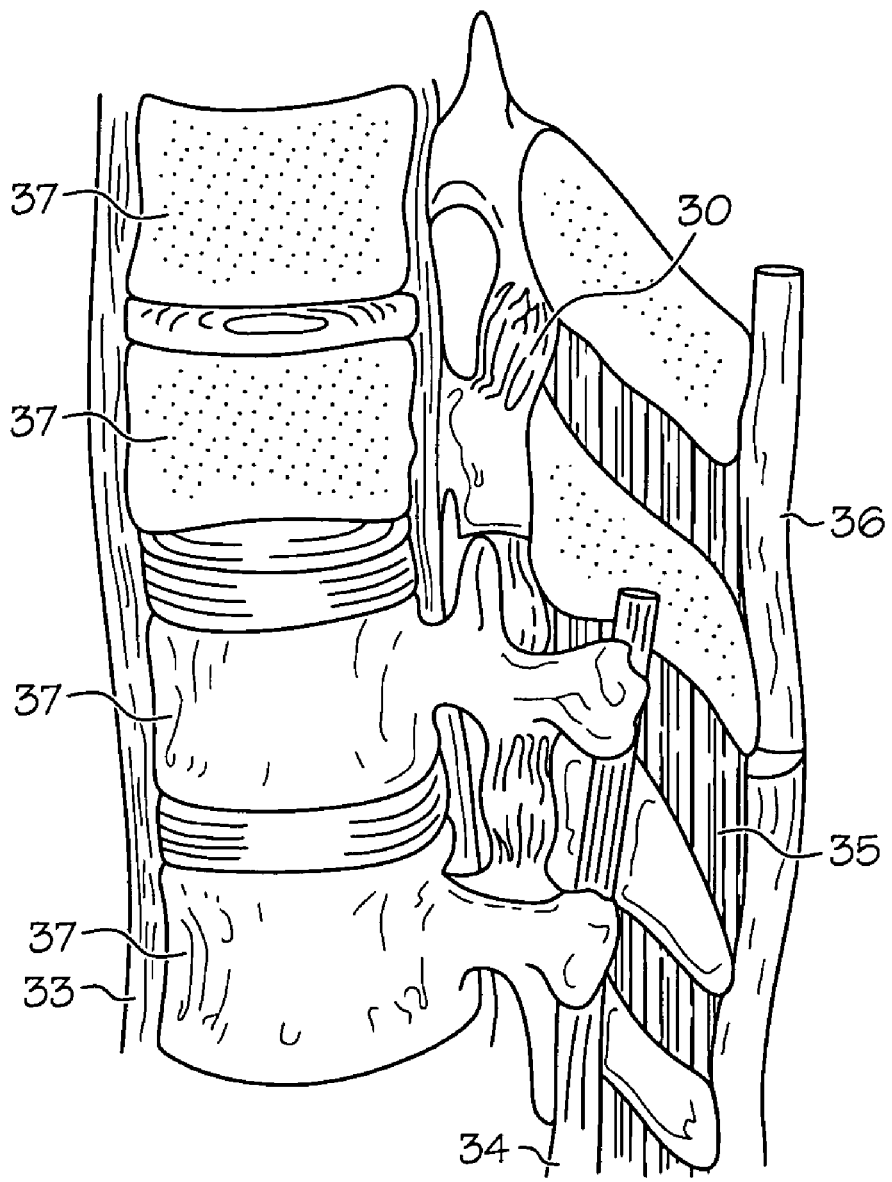
FIG. 2 illustrates various anatomical features of a portion of the vertebral column, including connective tissue, such as the ligamentum flavum through which medical leads are passed into the epidural space for electrical stimulation or sensing of the nerves of the spinal cord.
Figure 3:
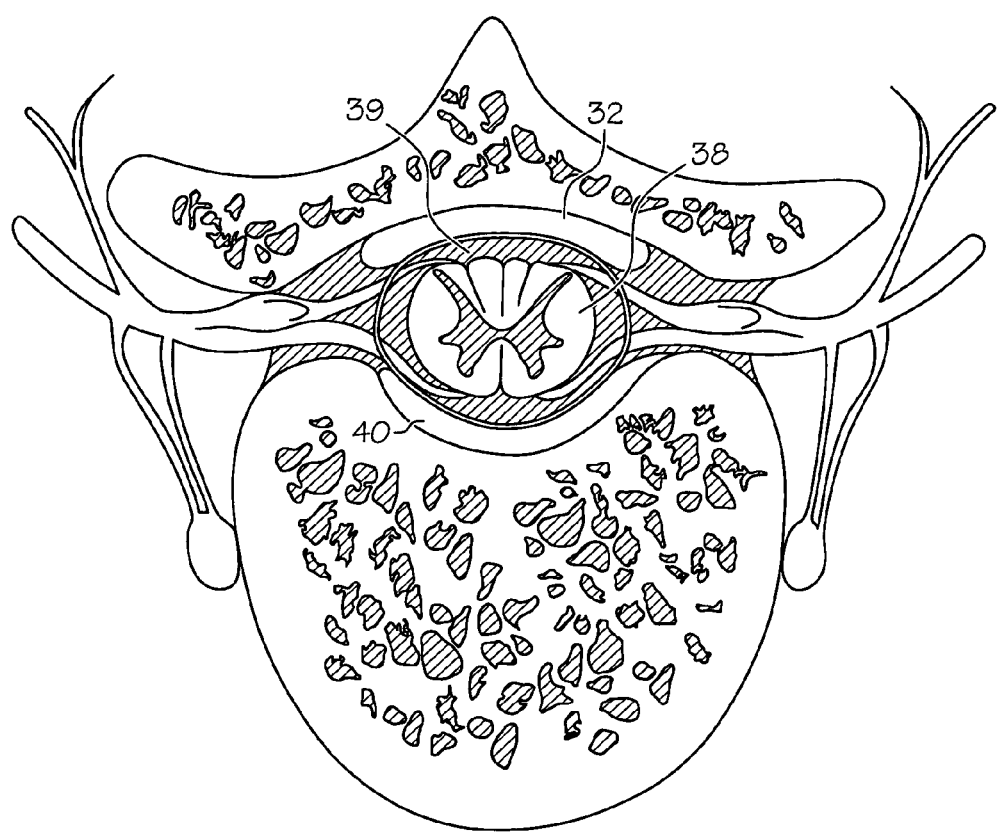
FIG. 3 is a cross sectional view along a transverse plane of a vertrebral column.
Figure 4:
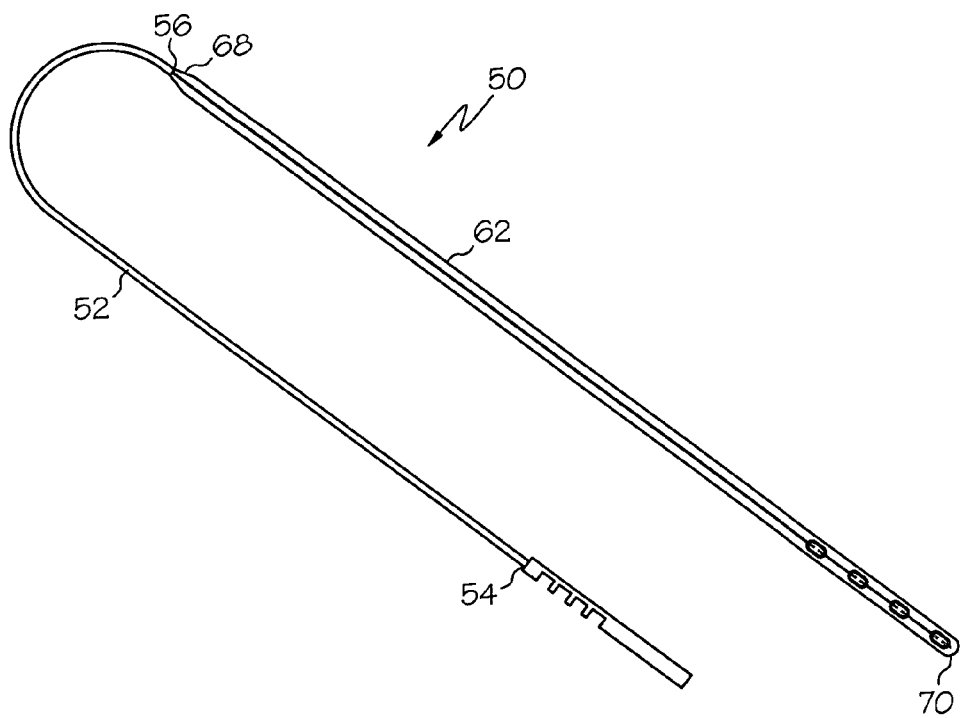
FIG. 4 is a plan view of an exemplary paddle-style medical lead of the invention.
Figure 5:
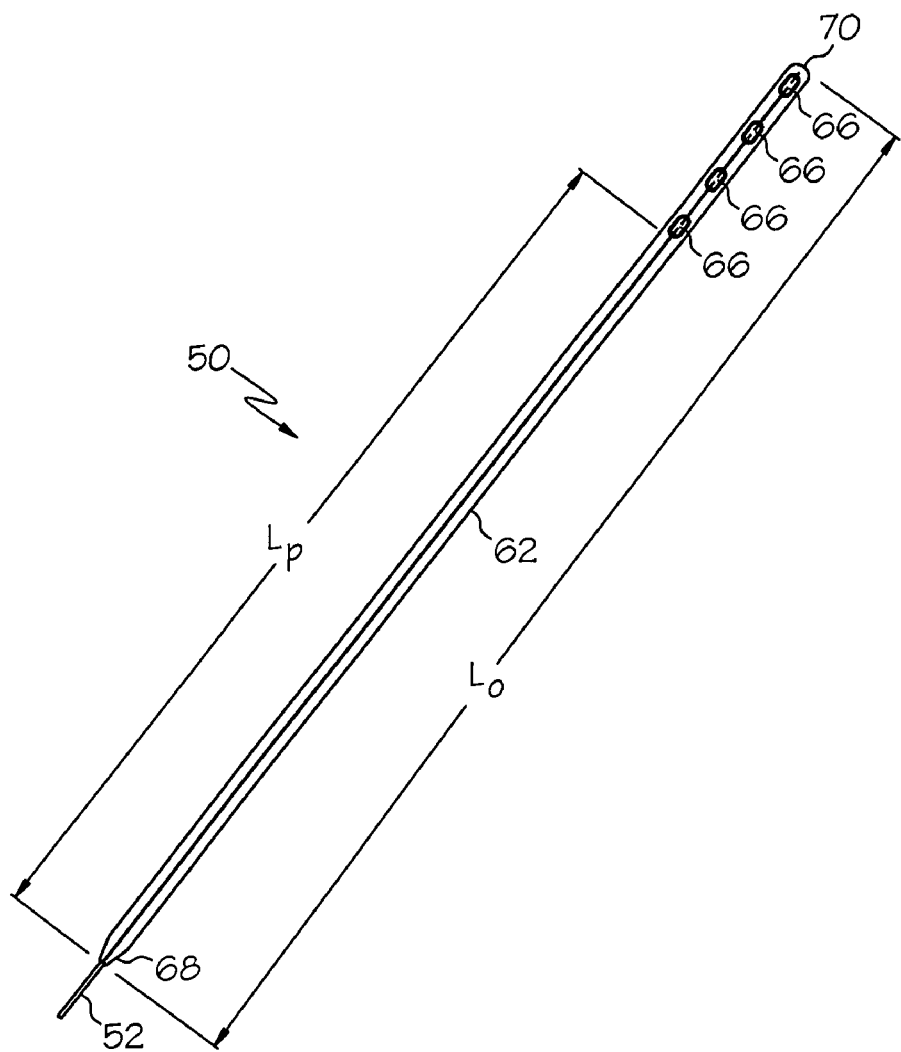
FIG. 5 is a plan view the paddle of FIG. 4.
Figure 6:
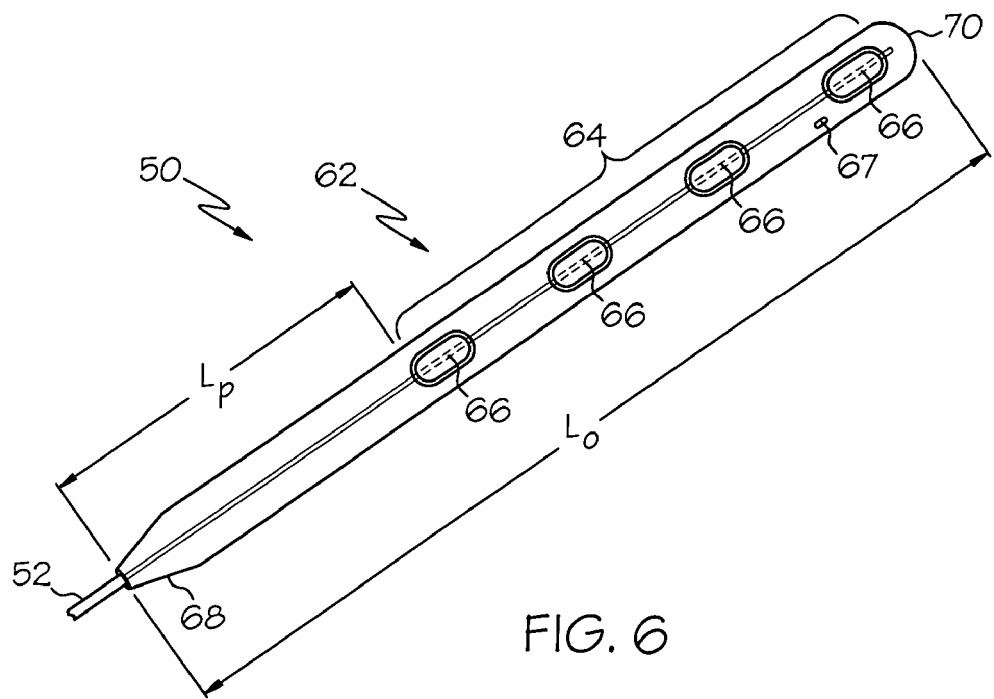
FIG. 6 is a partial view of a second exemplary embodiment of the paddle-style lead, illustrating among other things an orientation marker.

FIGS. 2 and 3 illustrate details of spinal or vertebral anatomy, including connective tissue, such as the ligamentum flavum 30 (FIG. 2) and the posterior epidural space 32 (FIG. 3). Exemplary embodiments of the medical lead 50 are adapted to be implanted through the ligamentum flavum 30 into the epidural space 32 into position for electrical spinal cord stimulation. FIG. 2 also illustrates, among other things, the anterior longitudinal ligament 33, intertransverse ligament 34, interspinal ligament 35, and supraspinal ligament 36, and, of course, vertebra 37. FIG. 3 also illustrates, among other things, the spinal cord 38, intrethecal space 39, and anterior epidural space 40.

FIGS. 4-8 show two exemplary embodiments of the paddle-style lead 50. The medical lead 50 comprises a generally round or tubular lead body 52 having proximal and distal ends 54 and 56, and at least one electrical conductor 58 (e.g., 4 or 8) extending between the proximal and distal ends. A connector or contact ring 60 is provided on the proximal end 54 of the lead body 52 in electrical communication with the electrical conductor 58. A generally flat paddle 62 is provided on the distal end 56 of the lead body 52.

An electrode array 64 is provided on the flat paddle 62 comprising at least one electrode 66 (e.g., four or eight electrodes) in electrical communication with the electrical conductor 58 (e.g., four or eight conductors corresponding to the number of electrodes). The paddle 62 has proximal and distal ends 68 and 70 and a length "$L_O$" extending between the proximal and distal ends. The electrode array 64 is displaced along the length of the paddle toward the distal end 70. For example, the portion of the flat paddle proximal of the electrode array has a length $L_P$ of at least 4 inches (100 mm), 3 inches (75 mm), 2 inches (50 mm) or 1½ inches (40 mm).

In one preferred exemplary embodiment, four conductors are provided with each comprising fluoropolymer insulated 0.005 diameter MP35N—Ag core cables. Four connectors or contact rings 58 may be configured to constitute, for example, an in-line cylindrical connector system for connection to a lead extension or IPG. Four electrodes may also be provided each comprising platinum/iridium. Such exemplary embodiments may have a total lead length of 25 cm to 100 cm, e.g., 30, 45 and 60 cm standardized lengths. Of course, other dimensions, materials and number of electrodes could be employed, and these are provided for purposes of illustration only.

Figure 9:
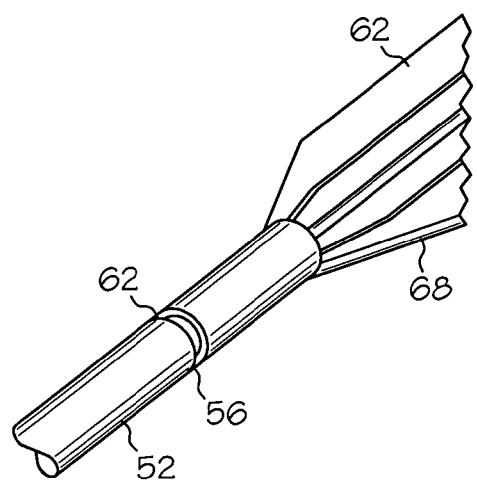
FIG. 9 is an exploded, partial view of the exemplary paddle-style medical lead of FIGS. 6-8, illustrating the location of a butt joint joining the paddle with the lead body.

One exemplary paddle 62 may have a nominal length of 8 inches (20 cm), nominal width of 0.15 inches (3.8 mm), and a nominal thickness of 0.04 inches (1 mm). The paddle 62 may be formed, for example, of material including polyurethane, and in one exemplary embodiment is formed of generally transparent polyurethane material The proximal end 68 of the flat paddle 62 preferably tapers down to the diameter of the lead body 52 as illustrated in FIGS. 4, 5, 6 and 8. FIG. 9 illustrates the butt joint 69 that may be used between the paddle 62 and the lead body 52. The butt bond 69 may be formed, for example, with urethane adhesive.

Figure 7:
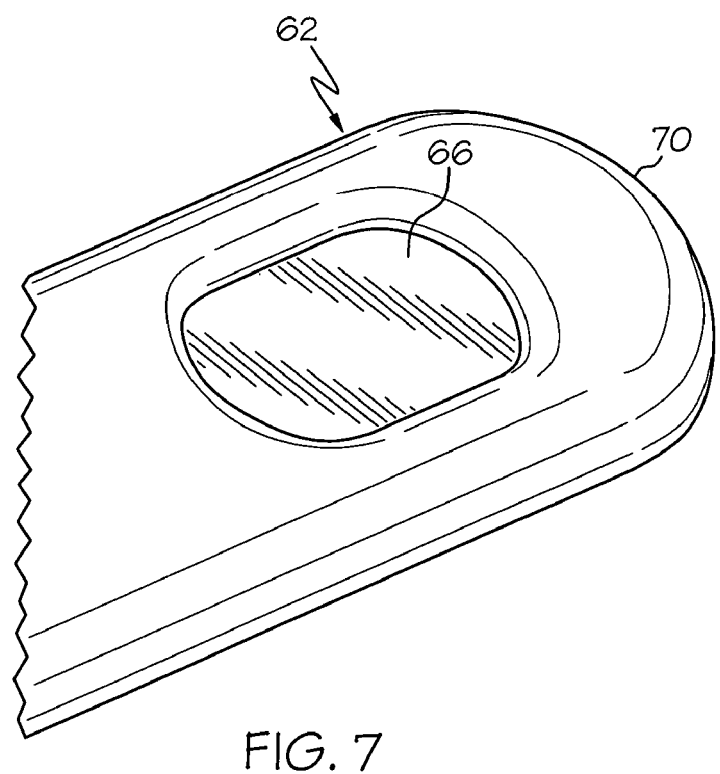
FIG. 7 is an enlarged view of a portion of the exemplary medical lead of FIG. 6, illustrating features of an exemplary electrode and paddle.
Figure 8:
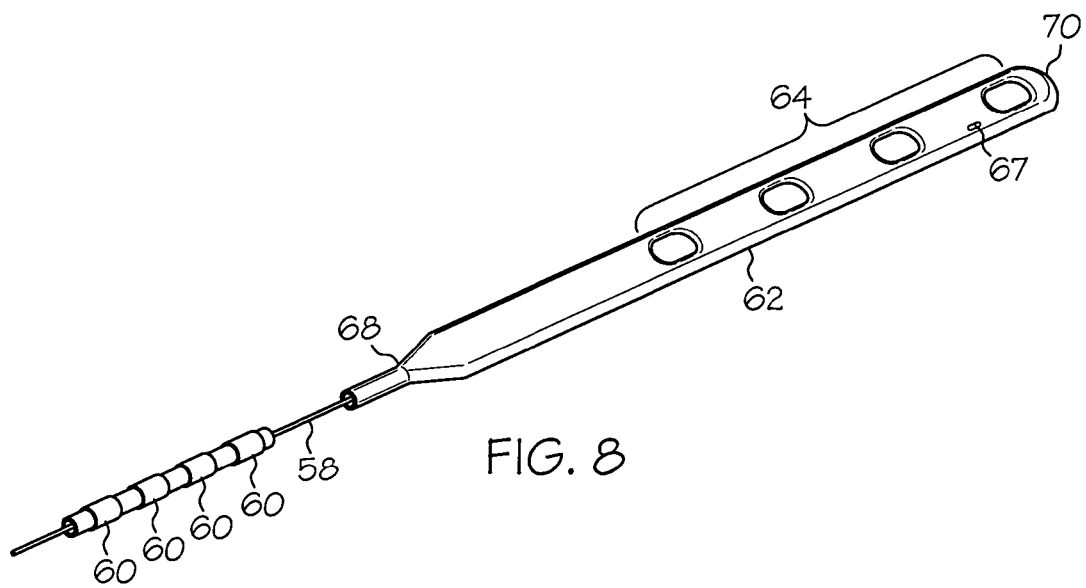
FIG. 8 is an exploded, partial view of the exemplary paddle-style medical lead of FIGS. 6 and 7.

The electrodes 66 may be recessed relative to the surface of the paddle as illustrated in FIG. 7, or co-planer with the surface. Examples include recessing the electrode 0.010 inches (0.25 mm) from the surface with the electrode having a surface area of approximately 6 mm$^2$.

An identification or orientation marker 67 (FIGS. 6 and 8) may be provided on the paddle 62 to indicate to physicians which side of the electrode plate is exposed versus insulated during and after implant. This may be helpful, for example, to determine whether the lead 50 has flipped or twisted during implantation. For example, an orientation marker 67 for determining orientation of the lead 50 may include fluoroscopically viewable material, such as radio-opaque material (e.g., platinum or platinum/iridium alloy). Since the electrode array 64 of at least one exemplary embodiment of medical lead comprises electrodes 66 exposed only through the first major surface of the paddle 62, the orientation marker 67 may be employed to provide a definite indication of the direction the paddle 62 (and electrode array 64) is facing.

For example, the paddle 62 may be considered as defining an imaginary longitudinal center line, and the orientation marker 67 may comprise a discrete radio-opaque marker 63 displaced from the longitudinal center line. When fluoroscopically viewing an implanted medical lead, the orientation of the paddle 62 may be determined by noting on which side of the imaginary center line the orientation marker 67 appears to be positioned.

In an exemplary embodiment, the orientation marker may comprise radio-opaque material arranged in an asymmetric manner with respect to the width of the paddle. As an alternative example of this embodiment, the orientation marker may comprise radio-opaque material dispersed in the paddle in an asymmetric manner with respect to the width of the paddle. Such radio-opaque material may be dispersed, for example, substantially uniformly in an asymmetric portion arranged asymmetrically with respect to the width of the paddle. The orientation of the implanted paddle may be determined by viewing an apparent asymmetric position of the orientation marker on the paddle, and determining, based on the apparent asymmetric position of the orientation marker, which direction the paddle is facing.

In a preferred exemplary embodiment, the orientation marker 67 is coded to identify the model or serial number of the lead 50. The code would preferably be fluoroscopically visible after implantation of the lead 50.

Figure 10:
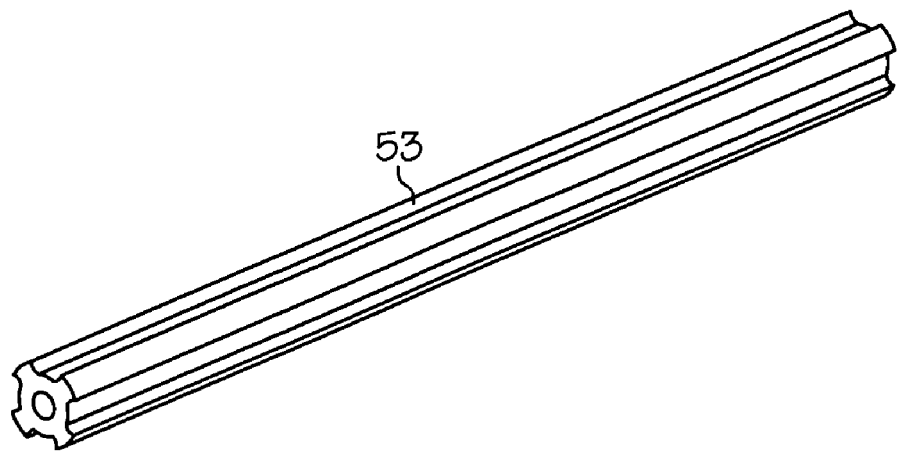
FIG. 10 is a perspective view of an exemplary center strut, which is one of two alternative preferred exemplary structures for use in the lead body of the medical lead of FIGS. 6-9.
Figure 11:
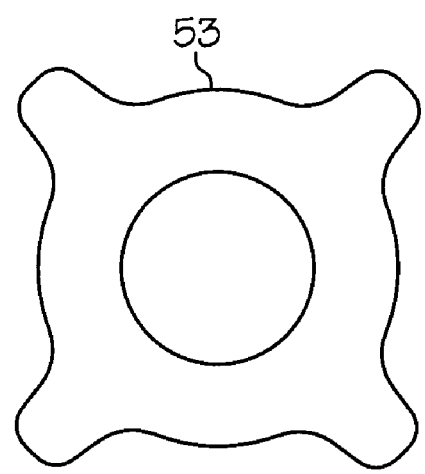
FIG. 11 is a cross sectional view of the exemplary center strut of FIG. 10, illustrating aspects of a center strut.
Figure 12:
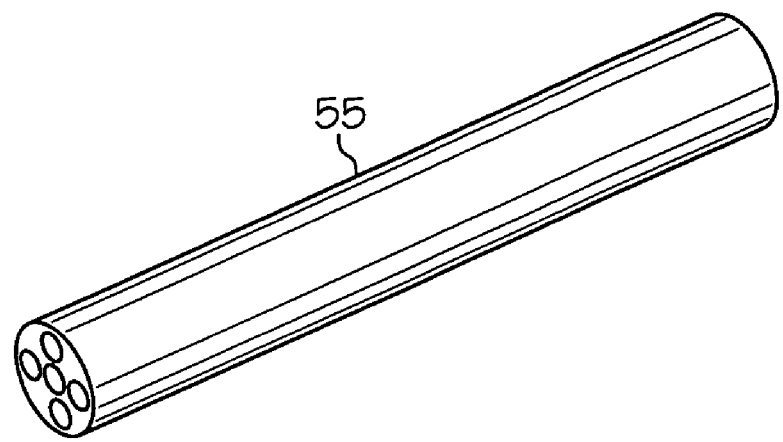
FIG. 12 is a perspective view of an exemplary pentalumen tubing, which is the other of two alternative preferred exemplary structures for use in the lead body of the medical lead of FIGS. 6-9.
Figure 13:
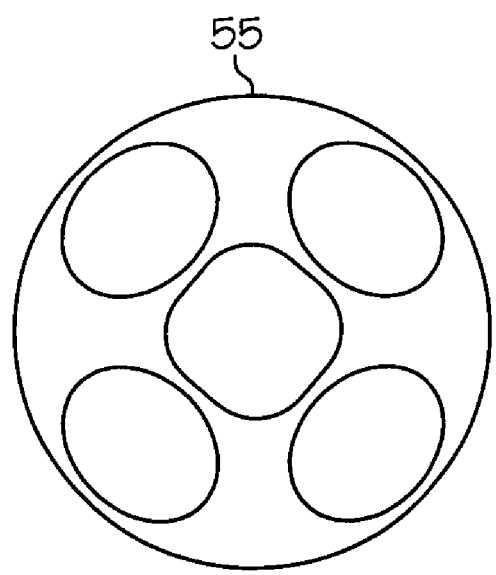
FIG. 13 is a cross sectional view of the exemplary pentalumen tubing of FIG. 12, illustrating illustrating aspects of pentalumen tubing.
Figure 14:
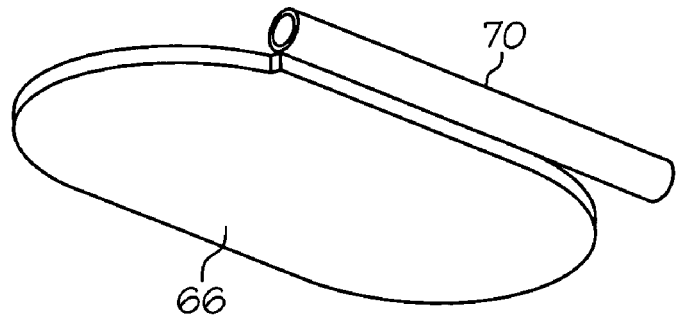
FIG. 14 is a perspective view of an exemplary embodiment of an electrode and crimp tube for electrically connecting a conductor wire with the electrode.
Figure 15:
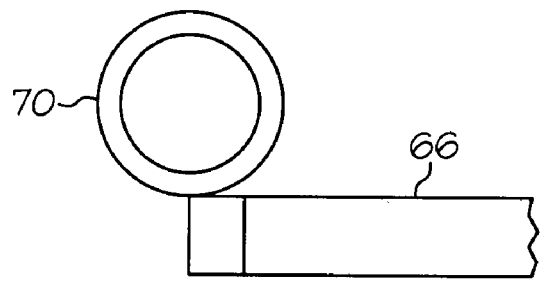
FIG. 15 is an end view of the electrode and crimp tube of FIG. 8.
Figure 16:
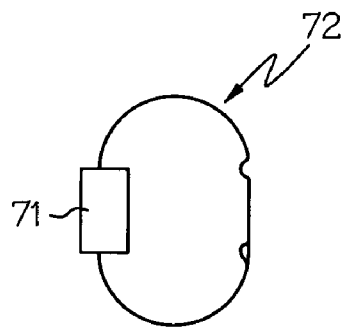
FIG. 16 is a back view of a second exemplary embodiment of an electrode with an integral crimp feature for connecting a conductor wire with the electrode.
Figure 17:
FIG. 17 is an end view of the exemplary electrode of FIG. 16.

Exemplary embodiments of the lead body 52 preferably includes a center strut 53 as illustrated in FIGS. 10 and 11, or pentalumen tubing 55 as illustrated FIGS. 12 and 13. The exemplary center strut defines a central stylet lumen and longitudinally extending channels for receiving conductor wires. The exemplary pentalumn tubing defiens a central stylet lumen and a plurality (e.g., 4) of longitudinally extending conductor lumens arranged radially outwardly from the central stylet lumen.

FIGS. 14-17 illustrate alternative preferred exemplary embodiments of means for electrically connecting a conductor wire to the electrode. The exemplary embodiment of FIGS. 14 and 15 involve use of a connector 70 (e.g., crimp tube 70), which is crimped to the conductor and welded, e.g., laser welded) to the lateral edge of the electrode 66. The exemplary embodiment of FIGS. 16 and 17 involves a crimp connector 71 that is an integral part of the electrode 72. The crimp connector 71 is shown in the form of a tab (also 71) that may be bent or crimped to connect the conductor to the electrode 72.

The exemplary embodiments of the connection means illustrated in FIGS. 14-17 are adapted to have strain or tension relief properties if the conductors are put under tension. Each of these means are illustrated as connecting the conductor to the lateral edge of the electrode 66 or 72 (relative to the longitudinal centerline of the paddle) such that tension along the conductor would tend to spin the electrode 66 or 72 thus tending to relieve such tension.

Figure 18:
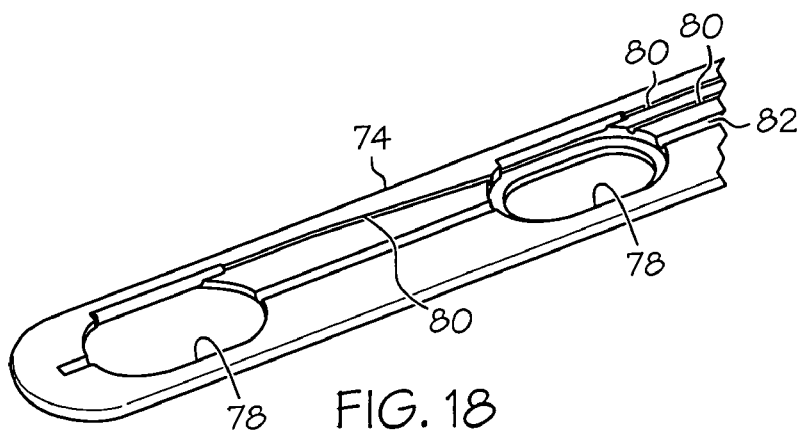
FIG. 18 is a perspective view of a half portion of an exemplary embodiment of the paddle, illustrating the connection of a conductor wire to the electrode via a crimp tube arranged along a lateral side of the electrode, the arrangement being such that tension tends to turn the electrode thus providing some additional strain relief.
Figure 19:
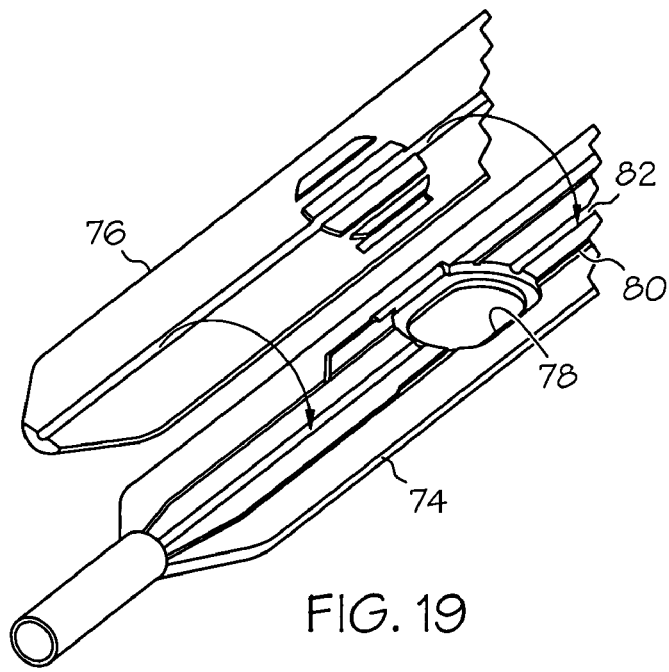
FIG. 19 is a perspective view of two half portions of an exemplary embodiment of the paddle, illustrating aspects of assembly of the paddle.
Figure 20:
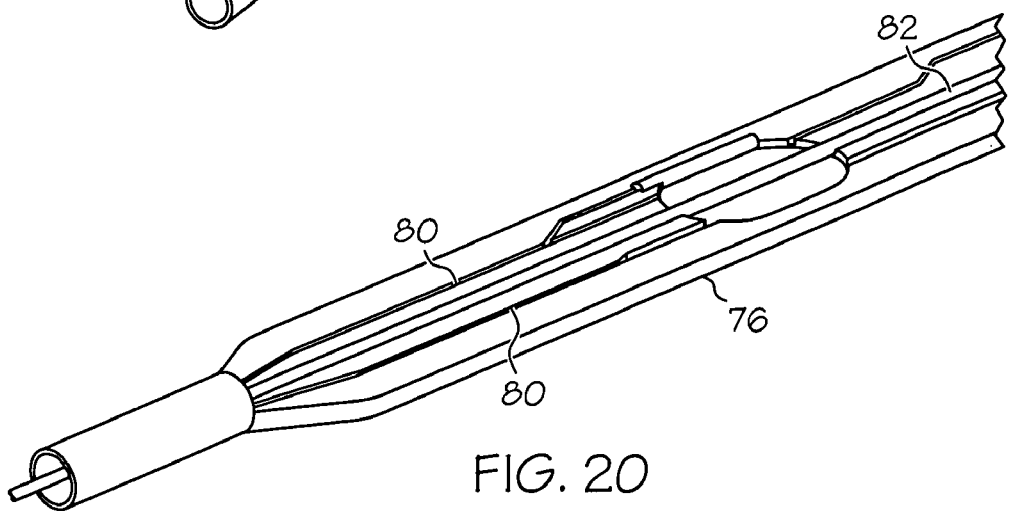
FIG. 20 is a perspective view of the paddle with one half portion removed to illustrate passage of a stylet.

The paddle 62 may be formed of two half sections 74 and 76 (e.g., "lower" paddle half 74 and "upper" paddle half 76) as shown on FIGS. 18-20. For example, the half sections 70 and 72 may be formed of polyurethane. Electrode receiving apertures 78 may be provided (e.g., molded) in the lower paddle half 74. Conductor wire paths 80 and stylet-lumen-forming channels 82 may be formed (e.g., molded) in one of both of the lower and upper paddle halves 74 and 76.

The sections 74 and 76 are bonded together (e.g., with polyurethane adhesive) after assembly and connection (e.g., laser welding and/or crimping) of the electrodes 66 and conductors. The stylet-lumen forming channels 82 thus form a stylet lumen.

Figure 21:
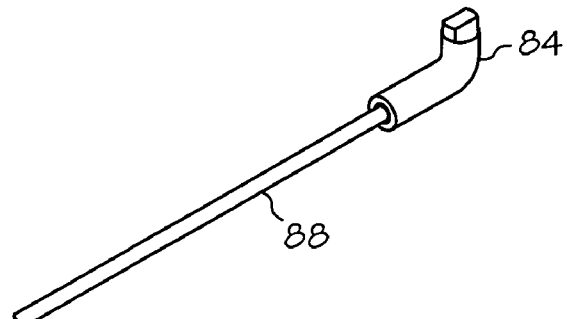
FIG. 21 is a perspective view of an exemplary embodiment of a conductor and crimp sleeve for use in connecting to a proximal contact.
Figure 22:
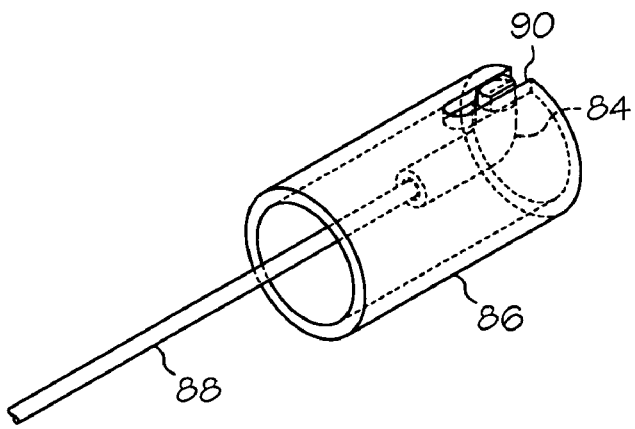
FIG. 22 is a perspective view of an exemplary embodiment of a conductor and crimp sleeve of FIG. 13 shown in relation with an exemplary proximal contact.

FIGS. 21 and 22 illustrate aspects of an exemplary embodiment of a crimp sleeve 84 for electrically connecting the proximal contacts 86 (e.g., contact ring) and conductor wires 88. A miniature conductor 88 is crimped to the sleeve 84, and the proximal contact 86 includes a slot 90 for receiving the crimp sleeve 84. In at least one example, the sleeve 84 is then bent and its end flattened to match the slot 90 in the contact 86, and the crimped cable/sleeve assembly is welded to the contact 86.

Figure 23:
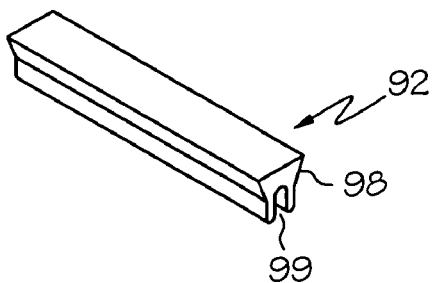
FIG. 23 is a perspective view of a second exemplary embodiment of a crimp sleeve for use in connecting a conductor to a proximal contact.
Figure 24:
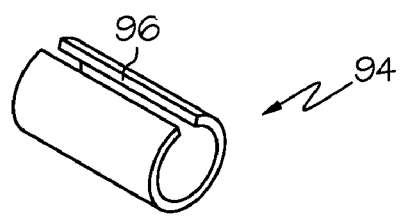
FIG. 24 is a perspective view of a second exemplary embodiment of a proximal contact for use with the exemplary crimp sleeve of FIG. 23.

FIGS. 23 and 24 illustrate aspects of a second preferred exemplary embodiment of a crimp sleeve 92 and proximal contact ring 94. The contact ring 94 is generally cylindrical and has a longitudinal slot 96 for receiving the flared contact-connecting portion 98 of the crimp sleeve 92, which may be welded, for example, in place. The crimp sleeve includes a conductor-wire-receiving channel 99, which may be crimped to retain the conductor wire. Exemplary alternatives to the channel 99 include without limitation a crimp-able lumen (not shown).

Figure 25:
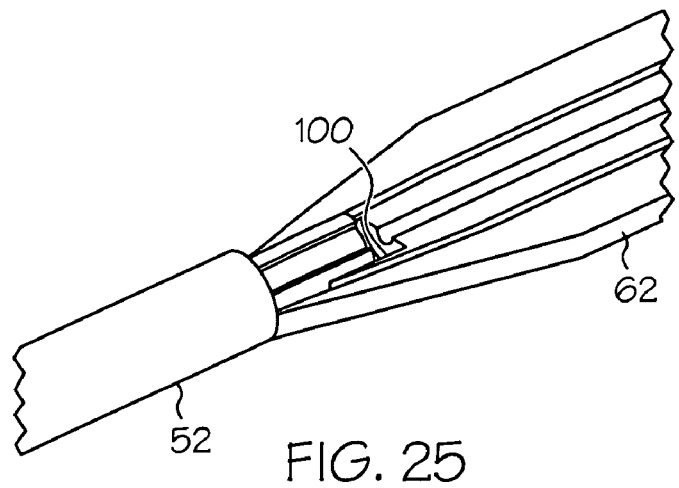
FIGS. 25 and 26 are perspective views of an exemplary embodiments of a proximal area of a lead and the interface between the lead body and lead paddle, illustrating location of adhesive to minimize tensile loading of electrical conductors, contacts and electrodes.
Figure 26:
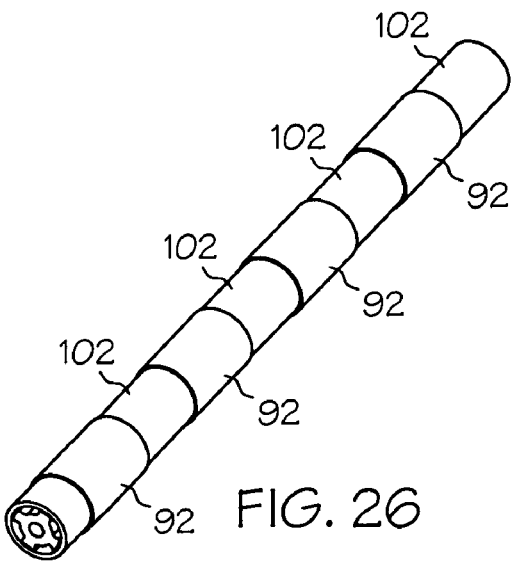
Figure 27:
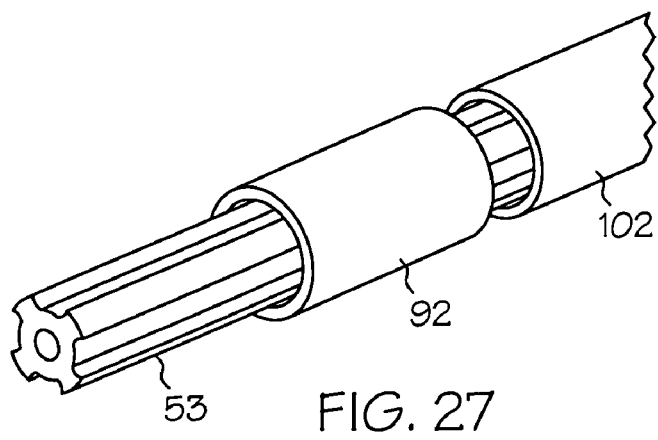
FIG. 27 is a perspective view illustrating an exemplary embodiment of the assembly of a proximal contact on an exemplary embodiment of a center strut of a lead.

FIG. 25 illustrates an example of where (e.g., at 100) the center strut 53 may be adhesively bonded to the proximal end of the paddle 62 (e.g., with urethane adhesive). FIG. 27 illustrates the distal end 56 of the body portion 52, which is bonded to the proximal end of the paddle at 100 in FIG. 25.

Figure 28:
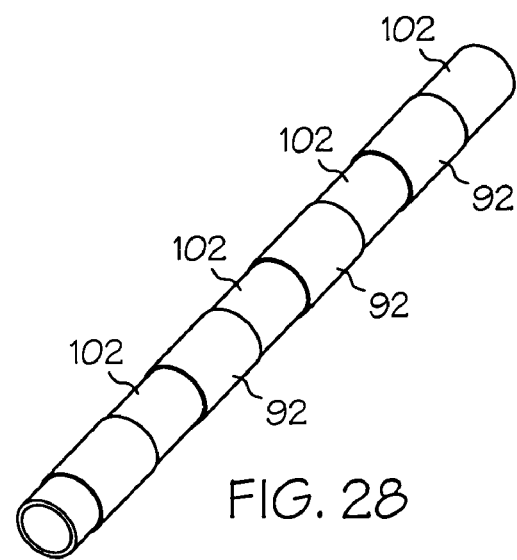
FIG. 28 is a perspective view illustrating electrically conductive proximal contacts separated by electrically insulative spacers.
Figure 29:
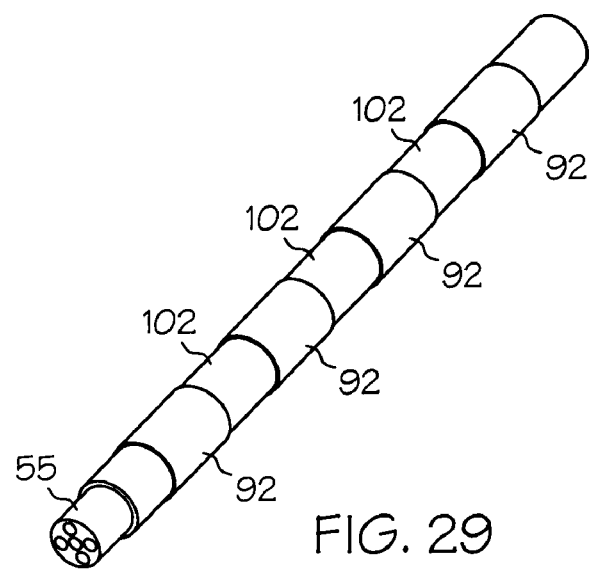
FIG. 29 is a perspective view illustrating electrically conductive proximal contacts separated by electrically insulative spacers arranged on pentalumen tubing.
Figure 30:
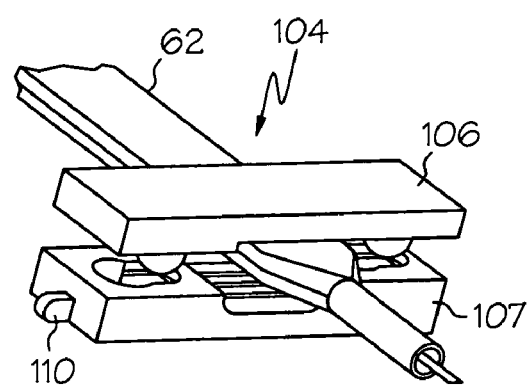
FIG. 30-33 are perspective views of an exemplary embodiment of an anchor for use with exemplary embodiments of the medical lead.
Figure 31:
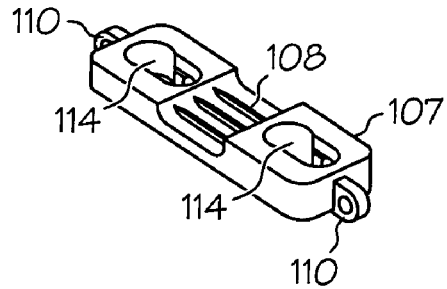
Figure 32:
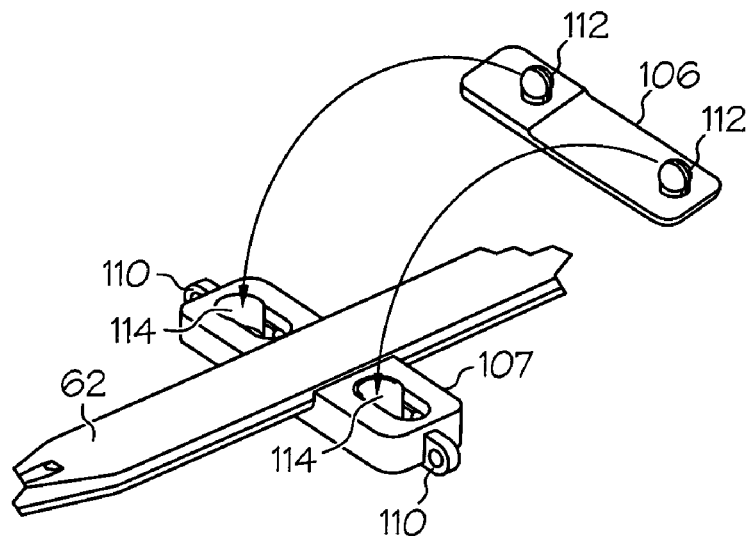
Figure 33:
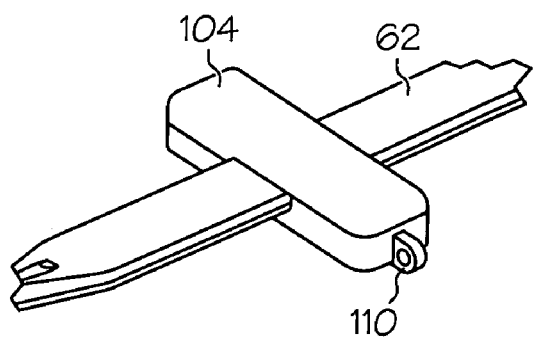

FIGS. 27-29 illustrate various exemplary details of the proximal contact portion and the assembly thereof. For example, FIG. 27 illustrates assembly of proximal contacts 92 on a center strut 53 alternating with assembly of an electrically insulative urethane spacer 102. FIG. 29 illustrates an exemplary arrangement of proximal contacts 92 and urethane spacer 102 arranged on a pentalumen tube 55.

An anchor, such as the anchor 104 illustrated in FIGS. 30-33, may be provided for clamping the flat paddle 62 and anchoring it to connective tissue, such as the ligamentum flavum 30. For example, two clamping jaws 106 and 107 of the anchor 104 are adapted to clamp the major surfaces of the flat paddle 62. One or both of the clamping arms 106 or 107 may be provided with at least one rib, but preferably a plurality of ribs 108 (e.g., 3), adapted to engage the flat paddle 62 and retain it in position. Suture loops 110 may be provided to suture the anchor 104 to connective tissue. The clamping arms 106 and 107 are preferably separable, with the clamping arms 106 and 107 being provided with mating knobs 112 and cavities 114 or other features for attaching the clamping arms 106 and 107 together.

Figure 34:
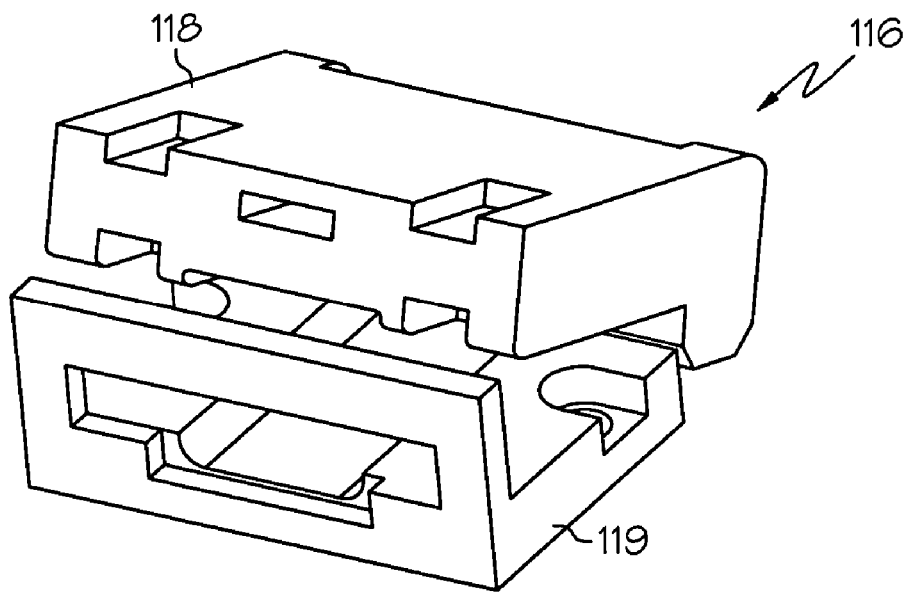
FIGS. 34 and 35 are perspective views of additional exemplary embodiments of an anchor for use with exemplary embodiments of the medical lead.
Figure 35:
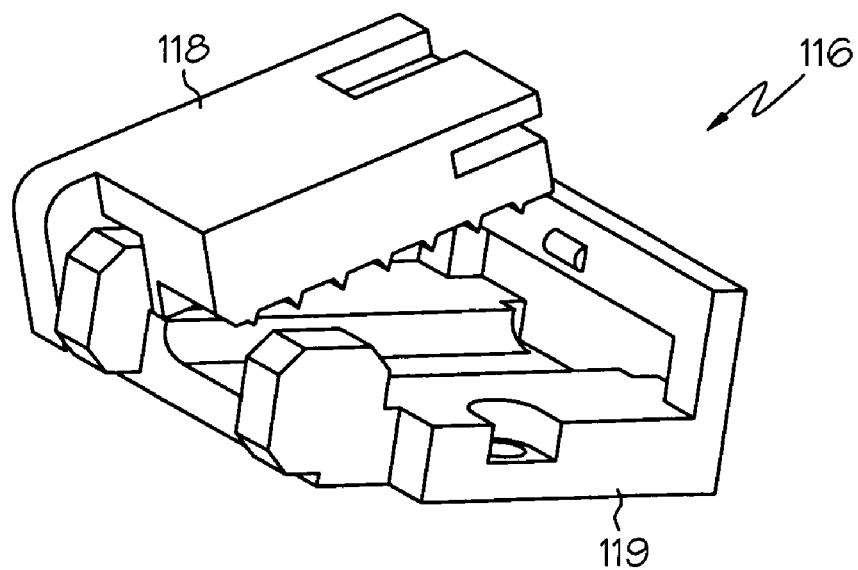

FIGS. 34 and 35 illustrate alternative exemplary embodiments of an anchor 116 in which the halves or jaws 118 and 119 pivot relative to one another in a claim shell fashion to anchor the lead 50. This embodiment may employ mating knobs and ribs as discussed with respect to the embodiment of FIGS. 30-33.

Figure 36:
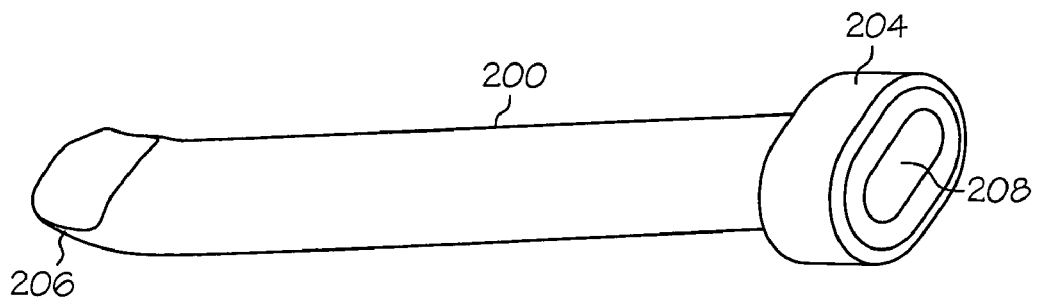
FIG. 36 is a perspective view of an exemplary embodiment of a needle, which has a flattened or oblong cross section for insertion of exemplary embodiments of the medical lead.
Figure 37:
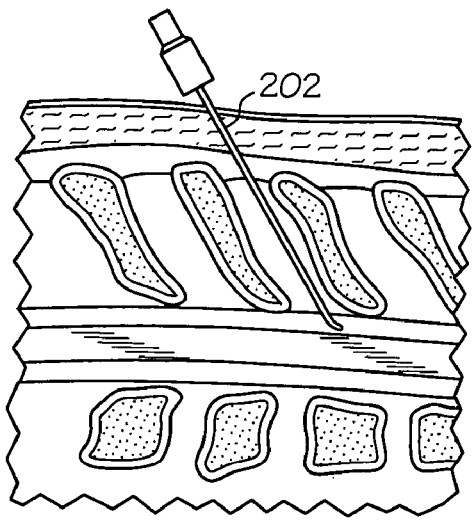
FIG. 37 is a vertical cross section view along a sagittal plane illustrating use of the needle of FIG. 36 to place a lead epidurally.
Figure 38:
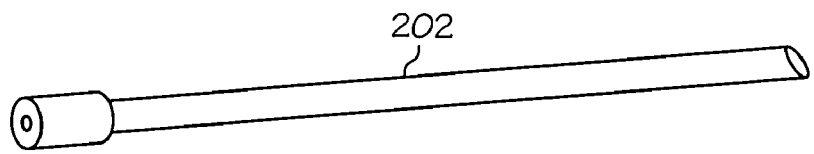
FIG. 38 is a perspective view illustrating an exemplary embodiment of a stylet for use in the oblong needle of FIGS. 36 and 37.

FIGS. 36-38 illustrate a preferred embodiment of a needle 200 and stylet 202 for use in exemplary embodiments of a procedure for introducing a paddle style lead 50 within the spinal column area, such as the epidural area, as depicted in FIG. 37. Alternative exemplary embodiments may into or near other nervous system structures, central or peripheral, such as intracranial nervous system structures or peripheral nerves.

As illustrated in FIG. 37, the needle assembly may be inserted into the spinal column area (e.g., epidurally). In an exemplary embodiment of the needle assembly, the lumen of the needle 200 has an oblong cross section sized to insert a paddle style lead 50 and has a curve at the distal end of the needle 200. U.S. Pat. Nos. 6,249,707 and 6,309,401, and EP 1 048 270, are incorporated herein by reference in their entirety, and particular note is made of the flattened needle, which may be used with certain exemplary embodiments of the medical lead disclosed herein.

The needle 200 comprises a body having a proximal end 204 and a distal end 206 and an inside lumen 208. The lumen 208 has an oblong cross section. The oblong cross section of the lumen 208 is adapted to receive a stylet 202 (FIG. 30) and a paddle style lead 50. The cross section of the lumen 208 is such that the width is greater than the height. A typical width for the lumen cavity to receive a paddle style lead 50 may be 2.5 mm to 12 mm (0.1" to 0.5") with a height of 1.4 mm to 2.0 mm (0.055" to 0.079"). The needle 200 may be made of stainless steel or other suitable materials. The needle 200 may also be adapted to insert multiple wire leads. Advantageously, the present invention allows a paddle lead to be inserted percutaneously without requiring the lead 50 to be rolled/contorted to fit the geometry of the needle lumen 208.

The needle 200 is further defined by an introducer portion (also 206) at the body distal end 206. The introducer portion 206 has a top side and a bottom side is shaped to allow for penetration of a patient's skin and other tissue. Typically, an epidural, Tuohy or modified Tuohy needle may be used. The top side of the introducer portion 206 has an orifice to allow the paddle style lead 50 to exit the lumen 208 of the needle 200 within the spinal column area after insertion of the needle 200. The introducer portion 206 may have the orifice at the distal end perpendicular to the lumen 208. A preferred exemplary embodiment of the needle 200 has an introducer with a curvature. The curvature extends from the bottom side of the introducer 206 to the top side of the introducer to facilitate and guide the paddle style lead 50 during insertion. The radius of curvature for the introducer 206 may be, for example, approximately 0.9". Other curvatures may also be used.

FIG. 38 illustrates a perspective view of the stylet 202 having a proximal end that is adapted to mate with the needle hub. The stylet 202 has a length nearly equivalent to the length of the body of the needle 200. The stylet 202 has a distal tip shaped for matching with the orifice of the introducer of the needle 200. A handle end is affixed to a proximal end of the stylet 202. In the preferred embodiment, the stylet 202 fills the entire orifice of the introducer 206 to prevent any skin or other tissue from entering the lumen 208 during insertion within the patient.

In at least one preferred exemplary embodiment, the stylet 202 may be constructed of an elastomeric material, or deformable material that is sufficiently flexible and resilient or redeformable to allow the stylet 202 to be removed from the needle 200 even where the needle 200 has been subjected to plastic deformation. Alternatively, the stylet 202 may be formed of stainless steel.

Figure 39:
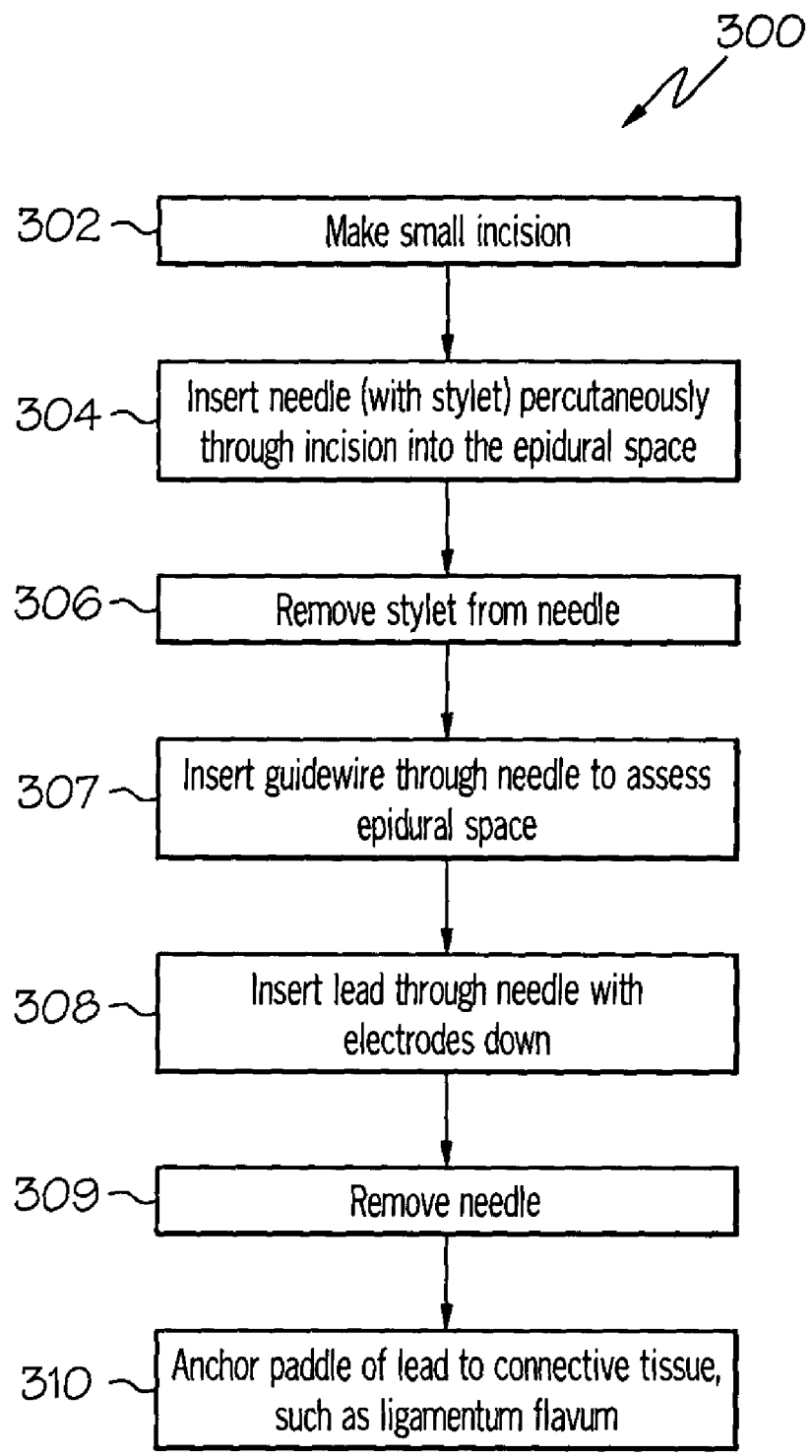
FIG. 39 is a flow chart illustrating an exemplary embodiment of a method of percutaneously implanting a medical lead.

FIG. 39 illustrates a general flow diagram of an exemplary preferred method 300 of use or implantation of the implantable paddle-style medical lead 50. The method 300 generally follows these steps: make small incision 302; insert needle (with stylet) percutaneously through incision into the epidural space 304; remove stylet from needle 306; insert guidewire through needle to assess epidural space 308; insert lead through needle with electrodes down 310; remove needle 312; and anchor paddle of lead to connective tissue, such as ligamentum flavum 314.

Thus, exemplary embodiments of the paddle-style medical lead and method are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A medical lead for electrical stimulation of a spinal cord, the medical lead comprising:
    a generally flat paddle, the paddle including first and second major surfaces, a proximal end and a distal end, the proximal end being joined to a distal end of a body of the lead, and the paddle defining an imaginary longitudinal center line;
    an electrode array comprising a plurality of electrodes, each electrode of the array being located on the longitudinal center line defined by the paddle, and being exposed through the first major surface and insulated by the second major surface, thereby having directional electrical field properties relative to the first and second major surfaces of the paddle, the electrode array being displaced longitudinally from the proximal end of the paddle such that a portion of the paddle that is free of electrodes extends proximally from the electrode array to the proximal end of the paddle, over a length such that the portion that is free of electrodes is configured to extend through connective tissue so that the proximal end of the paddle is positioned outside an epidural space when the entire electrode array is positioned within the epidural space alongside the spinal cord, the length being at least 40 mm; and
    an orientation marker being displaced from the longitudinal center line, on one side thereof, from every electrode of the electrode array, and longitudinally from the portion of the paddle that is free of electrodes, such that the orientation marker is configured to be positioned in the epidural space, with the entire electrode array, when the proximal end of the paddle is positioned outside the epidural space, the orientation marker including radio-opaque material such that, when the orientation marker is viewed under fluoroscopy, as being on a particular side of the longitudinal center line, the direction in which the first major surface of the paddle faces can be determined in order to ensure spinal cord stimulation.

2. The medical lead of claim 1, wherein each electrode of the electrode array is recessed relative to the first major surface.

3. The medical lead of claim 1 wherein the orientation marker is coded to identify the model or serial number of the lead.

4. The medical lead of claim 1 wherein the radio-opaque material comprises platinum.

5. The medical lead of claim 1, wherein at least the portion of the paddle is formed of substantially transparent polyurethane material.

* * * * *